United States Patent
Cregan et al.

(10) Patent No.: US 7,776,586 B2
(45) Date of Patent: Aug. 17, 2010

(54) METHOD FOR ISOLATING CELLS FROM MAMMARY SECRETION

(75) Inventors: Mark Derek Cregan, Clarkson (AU); Peter Edwin Hartmann, Gooseberry Hill (AU)

(73) Assignee: CARAG AG, Baar (CH)

( * ) Notice: Subject to any disclaimer, the term of this patent is extended or adjusted under 35 U.S.C. 154(b) by 479 days.

(21) Appl. No.: 10/584,002

(22) PCT Filed: Dec. 15, 2004

(86) PCT No.: PCT/CH2004/000738

§ 371 (c)(1), (2), (4) Date: Jun. 22, 2006

(87) PCT Pub. No.: WO2005/061696

PCT Pub. Date: Jul. 7, 2005

(65) Prior Publication Data

US 2007/0059822 A1 Mar. 15, 2007

(30) Foreign Application Priority Data

Dec. 23, 2003 (WO) ............... PCT/CH03/00846

(51) Int. Cl.
 C12N 5/00 (2006.01)
 C12N 5/071 (2006.01)
(52) U.S. Cl. ................ 435/325; 435/366
(58) Field of Classification Search .......... 435/325, 435/366
 See application file for complete search history.

(56) References Cited

U.S. PATENT DOCUMENTS

2004/0029269 A1* 2/2004 Goldman et al. ............ 435/368
2005/0095708 A1* 5/2005 Pera et al. ................... 435/369

FOREIGN PATENT DOCUMENTS

WO  WO 02/064755 A  8/2002

OTHER PUBLICATIONS

Young et al. Aus. J. Zool. 45(4):423-433; 1997.*
Young et al. Aus. J. Zool. 45:423-433; 1997.*
Stingl et al. Breast Cancer Res. Treat. 67:93-109; 2001.*
Buehring, G. J. Dairy Sci. 73:956-963; 1990.*
Nghiem et al. Methods 28:25-33; 2002.*
Badcock et al. Cancer Res. 59:4715-4719; 1999.*
Draper et al. Curr. Opin. Obst. Gynecol. 14:309-315; 2002.*
Gordon, Paul R. et al; "Large Scale Isolation of CD133+ Progenitor Cells from GCSF Mobilized Peripheral Blood Stem Cells"; Blood vol. 98, No. 11; Part 1; Nov. 16, 2001 p. 657a, XP009029619; 43rd Annual Meeting of the American Society of Hematology, Part 1; Orlando, Florida, USA; Dec. 7-11, 2001.
Prusa Andrea-Romana et al: "Oct-4-expressing cells in human amniotic fluid: A new source for Stem Cell Research?" Human Reproduction (Oxford) vol. 18, No. 7, Jul. 2003; pp. 1489-1493 XP002277347.
Durcova G. et al. "Immunomagnetic Isolation of Mouse Embryonic Stem Cells From Heterogeneous Cell Population", Journal of Reproduction and Development, Fuchu JP, vol. 44, No. 1, 1998, pp. 85-89, XP001037970.
Eirew et al., "A method for quantifying normal human mammary epithelial stem cells with in vivo regenerative ability," Nature Medicine 14: 1384-89, 2008.

* cited by examiner

*Primary Examiner*—Fereydoun G Sajjadi
(74) *Attorney, Agent, or Firm*—McDonnell Boehnen Hulbert & Berghoff LLP

(57) ABSTRACT

The present invention relates to a method for isolating progenitor cells from a human body, inclusive of all cells with stem cell-like characteristics, in particular pluripotent or multipotent progenitor cells, wherein such cells are directly or indirectly derived from human mammary secretion, be it colostrum, mature milk, or dry period secretion from males or females, of said human body during at least one of the following periods: non-pregnant period, pregnant period, lactating period, involuting period. The present invention furthermore relates to preferred uses of such isolated cells.

16 Claims, 11 Drawing Sheets

Figure 2:
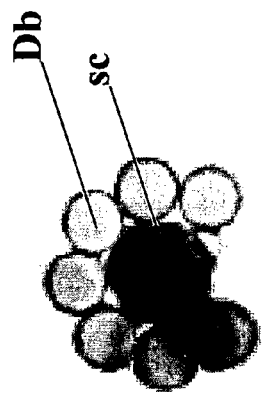

a) Fig. 2

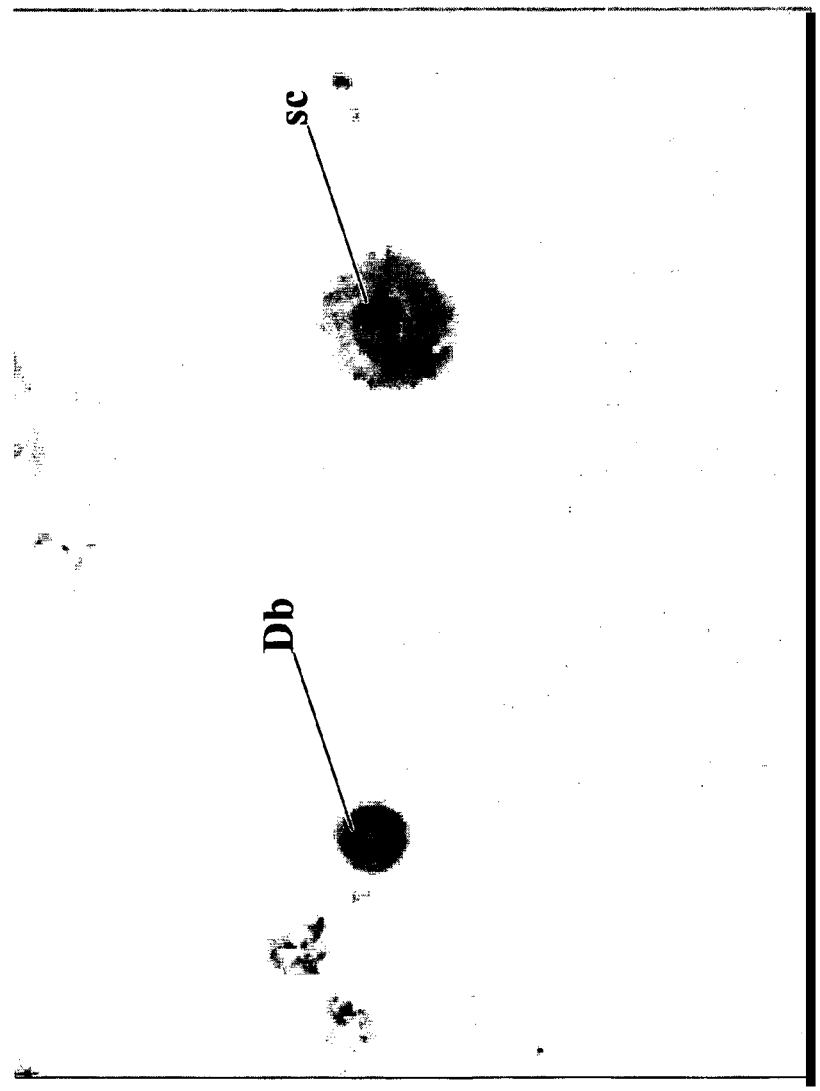

c)

a)

METHOD FOR ISOLATING CELLS FROM MAMMARY SECRETION

TECHNICAL FIELD

The present invention relates to a method for isolating cells from a human body, as well as uses of such cells.

BACKGROUND OF THE INVENTION

Stem cells are defined as clonogenic, self-renewing progenitor cells that can generate a wide variety of more specialised cell types via the process of differentiation. Classically, it has been believed that there are two distinct types of stem cell. Embryonic stem (ES) cells are derived from the inner mass of the blastocyst, are pluripotent and thus are capable of generating into all differentiated cell types within the body. The other sub-population of stem cells are derived from ES cells and are organ-or tissue-specific. These multipotent cells, also known as adult stem cells, were believed to be able to differentiate only into tissues from their organ of origin. An example of these multipotent cells are haematopoietic stem cells, which serve to continually regenerate the cells of the blood and immune system.

Stem cells have been isolated from a wide range of tissues, from those that have a high rate of ongoing cellular turnover, such as blood, cord blood, bone marrow, skin, intestine, and breast tissue, to those with a low turnover such as brain, skeletal muscle, and juvenile teeth. Irrespective of the tissue of origin, a long standing dogma has been that adult stem cells can only differentiate into the tissues from which they were derived. However recent work has demonstrated that upon exposure to a novel environment, organ-specific stem cells can overcome these intrinsic restrictions to transdifferentiate into other tissues. For example it has been shown that neural stem cells can transdifferentiate into blood cells, bone-marrow derived stem cells can transdifferentiate into muscle, brain, liver and heart cells, and skin derived stem cells can transdifferentiate into brain cells. Therefore it now appears likely that the dogma associated with developmental restriction of organ-specific stem cells is incorrect and it is feasible that these ES cells under appropriate enviromnental stimuli, can transdifferentiate into another cell type.

Human milk contains a mixture of different cell types. Secretory epithelial cells (lactocytes) are found in milk due to them sloughing off the basement membrane of the breast as a consequence of the pressure associated with the continued filling and emptying of the breast. Lactocytes account for approximately 10-20% of the total cell population. The majority of the remainder of cells found in human milk are leukocytes (immune cells such as lymphocytes, macrophages, monocytes, natural killer cells, basophils, eosinophils, and neutrophils), and are believed to be in milk to both protect the breast from infection and to provide immune protection for the infant. To date, these are the only cell types believed to be contained in milk.

SUMMARY OF THE INVENTION

The objective problem underlying the present invention is therefore to provide a new method for isolating progenitor cells from the human body. In this context, the term progenitor cells shall include all cells with stem cell-like characteristics, preferentially but not exclusively including pluripotent or multipotent progenitor cells like for example stem cells.

The present invention solves the above problem by deriving such cells directly or indirectly from human mammary secretion, be it colostrum, mature milk, or dry period secretion from males or females, of said human body during at least one of the following periods: non-pregnant period, pregnant period, lactating period, involuting period. In other words, here we demonstrate that surprisingly, progenitor cells can also be found in human lactation milk and that these cells have the potential to be utilised for the generation of tissues for the mother and infant. It has to be noted that not only human mammary secretion but generally mammary secretion from mammalian species can be used for the isolation of corresponding progenitor cells. It can unambiguously be shown by means of progenitor-cell-specific antibodies, that indeed mammalian secretion, i.e. for example human milk, comprises progenitor cells.

In a first preferred embodiment of the present invention, said progenitor cells are isolated from the mammary secretion in that non-cellular parts of the mammary secretion are separated from the cellular parts and that in particular non-pluripotent or non-multipotent cells are removed from cellular parts thus derived. The cellular parts of mammary secretion, apart from pluripotent cells may further comprise secretory epithelial cells, leucocytes and in particular nonhuman cells like bacterial cells. Those non-pluripotent cells are preferentially removed from the mammary secretion.

According to another preferred embodiment of the present invention, the mammary secretion during lactating periods is used for the isolation of the progenitor cells, wherein the mammary secretion during particular stages of mammary secretion such as: after beginning of individual feeding; versus end of individual feeding; lactation phase; preferably early lactation, is used.

A particularly useful and practicable way of isolating those progenitor cells from the secretion is possible if magnet beads are used. Those magnetic beads are to this end preferentially connected to progenitor-cell-specific antibodies allowing the attachment of the beads to the progenitor cells.

Typically, in a first step cellular components are washed out of the mammary secretion, in a second step said cellular components are stained with antibodies to the progenitor cell markers, and in a third step the progenitor cells are separated from the other cells directly or indirectly by means of the attached antibodies, preferentially, but not exclusively, by using the above-mentioned magnetic beads. To this end, the antibody-stained progenitor cells are attached to beads, preferably small iron beads, and the progenitor cells are extracted by means of the beads, preferably in case of small iron beads by using a magnet, and wherein subsequently the beads as well as if need be the antibodies are removed from the progenitor cells. This is for example possible by selecting the beads, which have been provided with specific antibodies attached to the beads, which antibodies selectively bind to the progenitor cells. To obtain the pure cells, subsequently the beads are removed from the progenitor cells, which is for example possible by means of enzymes cleaving the link between the beads and the antibodies. If the link between the beads and the antibodies is based on DNA, such cleavage can be effected by using Dnase, in case where the link between the beads and the antibodies is based on amino acid chains, proteinases can be used.

Surprisingly, while normally progenitor cells have to be cultured, i.e. grown, on very specific feeder layers, like for example mouse fibroblast feeder layers, the progenitor cells isolated in the present method do not need such specific feeder layers, but can generally be grown on other feeder layers based on for example the ones disclosed within the scope of the specific examples.

More specifically, the method of isolation comprises the following steps: (i) the whole human mammary secretion is subjected to centrifugation generally leaving a fat layer on top, a protein and carbohydrate rich supernatant beneath it, and at the bottom a pellet of cells; (ii) fat fraction and supernatant are removed; (iii) e.g. a buffer, such as, but not limited to, phosphate buffered saline, tris buffer saline, TBS and/or PBS, or media, such as, but not limited to, Williams media or RPMI Media, is added and the cells (not only comprising progenitor cells) are resuspended in the buffer / media and centrifuged as before, preferentially repeating this process 3 or 4 times, leaving a substantially pure cell pellet; (iv) the progenitor cells are separated from the cell pellet.

Preferentially, the separation of the progenitor cells from the cell pellet is carried out in the following steps:(v) the cell pellet is suspended in media, preferentially in RPMI media containing for example fetal calf (bovine) serum; (vi) this suspension is incubated with (magnetic) beads which have preferentially before been incubated with progenitor-specific antibodies (preferentially stem cell-specific antibodies, like anti-mouse IgG antibodies), which antibodies are attached to the magnetic beads via a small strand for example of DNA or amino acids, wherein the incubation of the cell suspension in these magnetic beads is preferentially carried our for 15 minutes at 4° C.; (vii) once the progenitor cells have bound to the magnetic beads a magnet is attached to the tube containing the cells/beads, thus attracting the progenitor cells connected with the beads to the magnet, whereas unbound cells are not and remain in the supernatant; (viii) removing the supernatant leaving only the progenitor cells bound to the beads via the progenitor cell antibody.

It has to be pointed out that other types of beads or generally separation means can be used which allow to selectively attach them to the progenitor cells. Such beads have to be separated from the progenitor cells, and to this end preferentially the following processing steps can be used: (ix) progenitor cells bound to the beads via the stem cell antibody are removed by an appropriate cleavage means, preferentially, in case of the antibody being attached to the beads via small strand of DNA, a by means of addition of a Dnase, (x) the beads are removed by attaching the magnet once more, such that the beads, no longer attached to the stem cells, are attracted to it; (xi) removing the supernatant now containing the isolated progenitor cells.

An alternative method of separation which is based on specific growth of pluripotent cells involves the following steps:

(i) a first step the whole human mammary secretion is subjected to centrifugation leaving a fat layer on top, a protein and carbohydrate rich supernatant beneath it, and at the bottom a pellet of cells.

(ii) in an optional second step, the cell pellet is washed in media. Preferably the cells are washed in RPMI media only.

(iii) in a third step the cells of the cell pellet are plated onto a cell culture treated device in growth media and are allowed to incubate. Preferably this incubation is carried out for 10-30 days, most preferably for 14-20 days.

(iv) the cells are harvested, i.e. they are detached from the support, preferably by trypsination. Subsequently the detached cells are washed, preferably using growth media solution.

(v) the harvested and washed cells are plated onto a reconstituted basement membrane preparation for growth, preferably up to confluence. In this last step, preferably a solubulized basement membrane preparation extracted from EHS mouse sarcoma is used, like e.g. Matrigel™ as available from BD Biosciences.

This method leads to cell cultures with a morphology which is typical for progenitor cells. The cells do not look like lactocytes and due to the growth media which is permissive for progenitor/stem cell/lactocyte growth, they cannot be bacterial cells.

The present invention furthermore relates to progenitor cells, which are preferentially pluripotent or multipotent progenitor (stem) cells, derived using a method as described above.

Additionally, the present invention relates to uses of such progenitor cells, for example for ex vivo, in vitro and/or in vivo applications. Without limiting the scope of the invention, such use may extend to the following specific examples or combinations thereof: creation of tissues or cells for the benefit of the mother and/or of the infant and/or of other individuals; subsequent gene therapy treatments or intrauterine foetal treatments; generation of cells, tissue, glands or organs for the treatment of disease; subsequent cloning or scientific research; one or several of the group of the following purposes: clinical, diagnostic, bioengineering, lactoengineering, breast tissue regeneration, breast reconstructive surgery, breast cosmetic or enhancement surgery, exocrine gland tissue regeneration and/or surgery.

Further embodiments of the present invention are outlined in the dependent claims.

SHORT DESCRIPTION OF THE FIGURES

Figure 1:
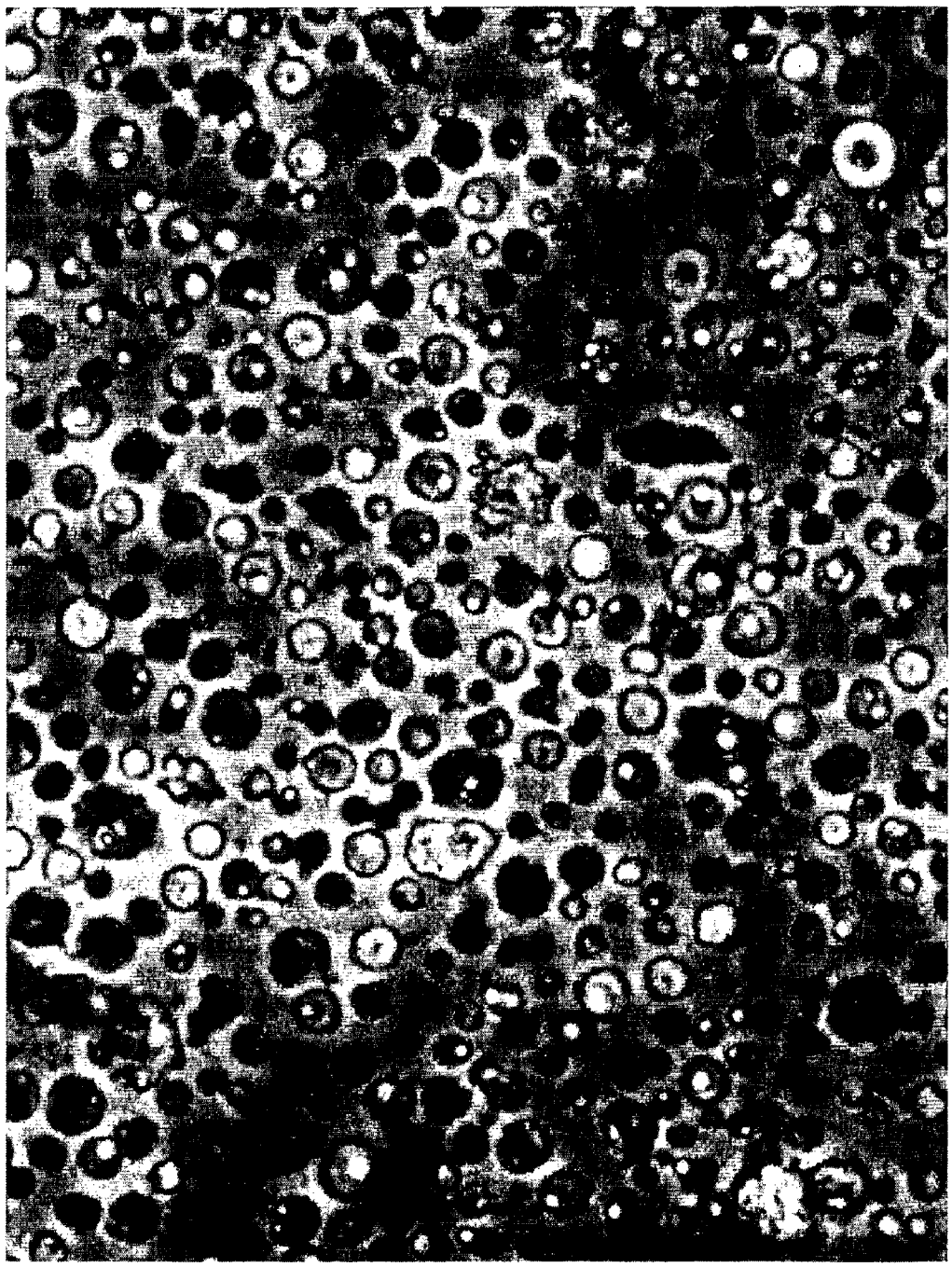
Figure 3:
Figure 4:
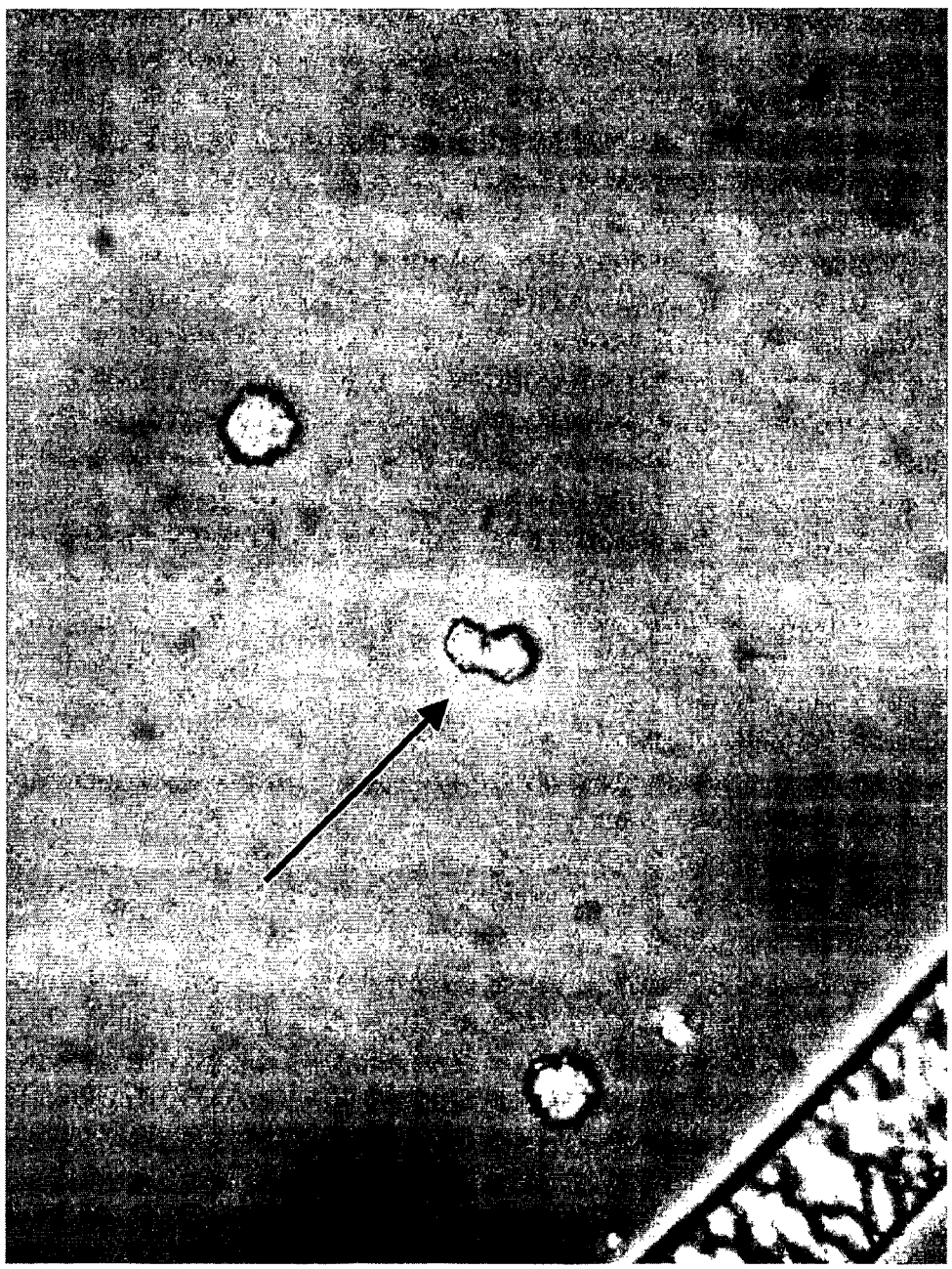
Figure 5:
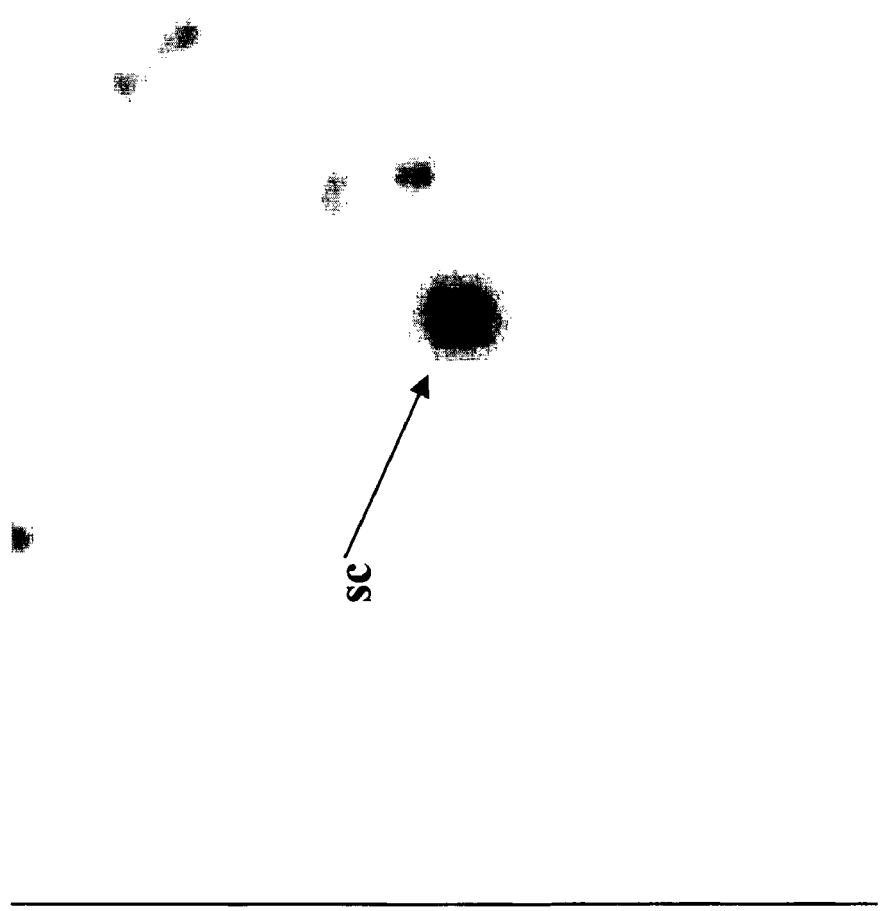
Figure 6:
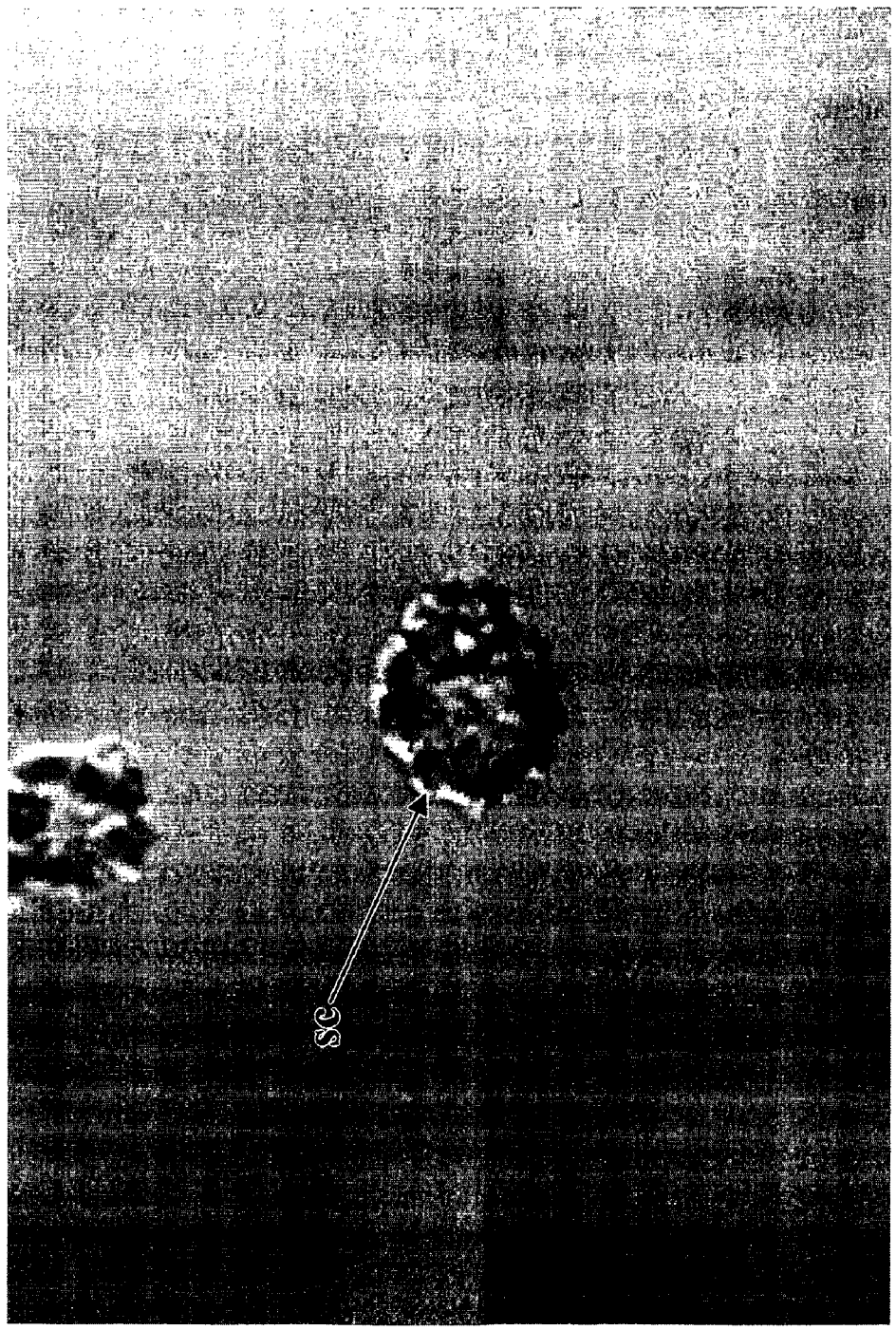
Figure 6:
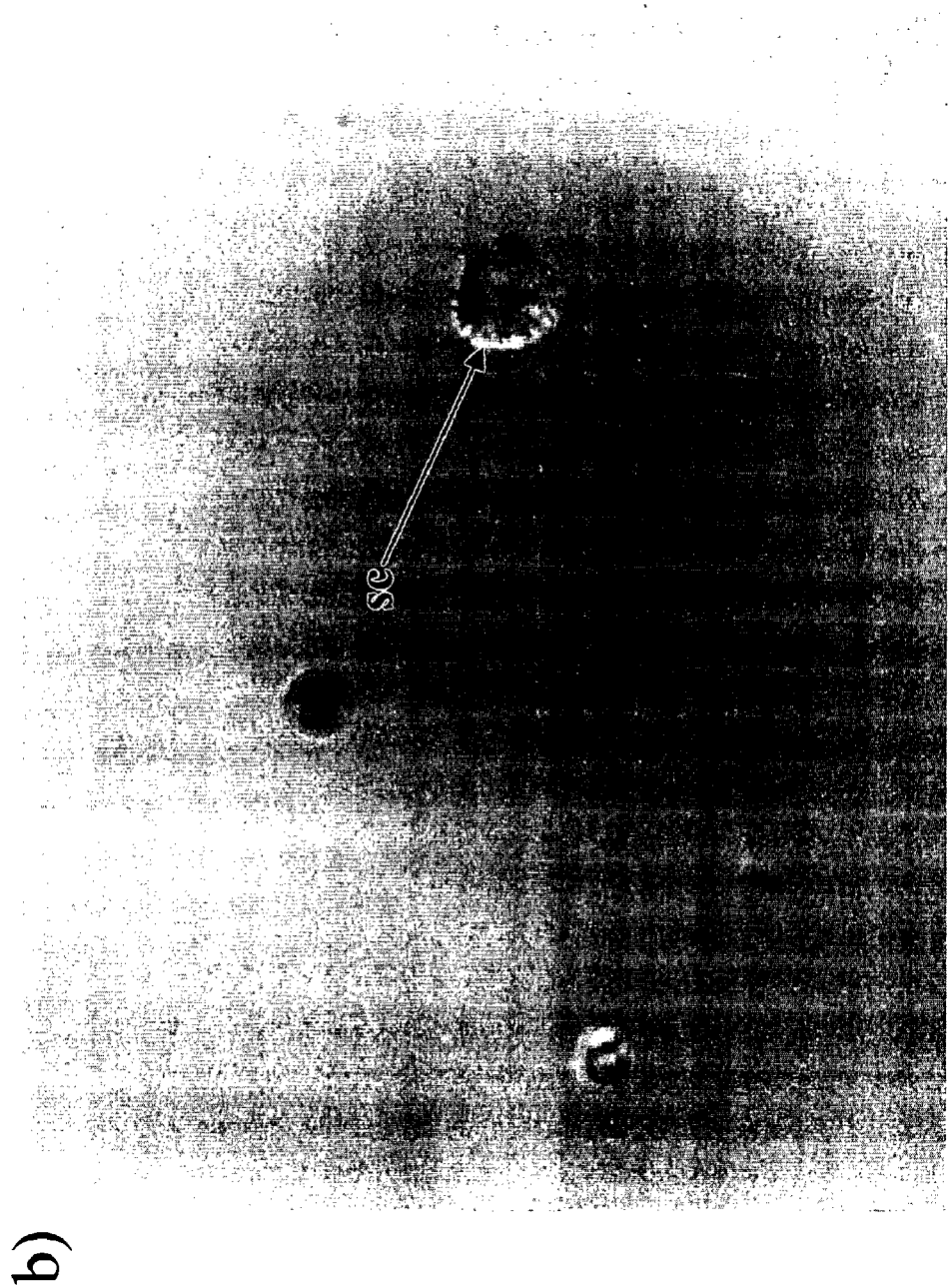

In the accompanying drawings preferred embodiments of the invention are shown in which:

FIG. 1 shows the total mixed cell population of human milk following removal of the fat and skim milk;

FIG. 2 shows the stem cells (sc) following their isolation from a total milk cell population. These cells have been cytospun onto microscope slides and stained with haematoxylin and eosin. FIG. 2a) and 2b) show a single stem cell (sc). FIG. 2c) shows a single stem cell still bound to the Dynabeads® (Db). The Dynabeads® (Db) are 4.5 µM in size, thereby permitting the approximate sizing of the stem cells to be 6-7 µM;

FIG. 3 following purification of the stem cells from a total milk cell population, the stem cells that are isolated can be cultured using a variety of culture conditions; this figure shows a single stem cell 1 day after being placed into culture;

FIG. 4 after 1 to 2 weeks in culture, the stem cells isolated from a total cell population begin to undergo cell division (mitosis); the arrow in this photo indicates a cell undergoing mitosis;

FIG. 5 after several months in culture, these cells do not appear to have differentiated into other cell types; this figure shows a stem cell after 2 months of culture which has been cytospun onto a microscope slide and stained with haematoxylin and eosin;

FIG. 6 after 2 months in culture the stem cells have not differentiated; this figure shows the stem cells isolated with the SSEA-4 (a) and Tra 1-60 (b) antibodies, following 2 months in culture; the cells were washed out of the culture medium and cytospun onto a microscope slide before being visualised on a confocal microscope with the SSEA-4 (a) and Tra 1-60 (b) antibodies conjugated to a fluorescently labelled secondary antibody (goat anti-mouse IgG conjugated to AlexaFluor-488).

Figure 7:
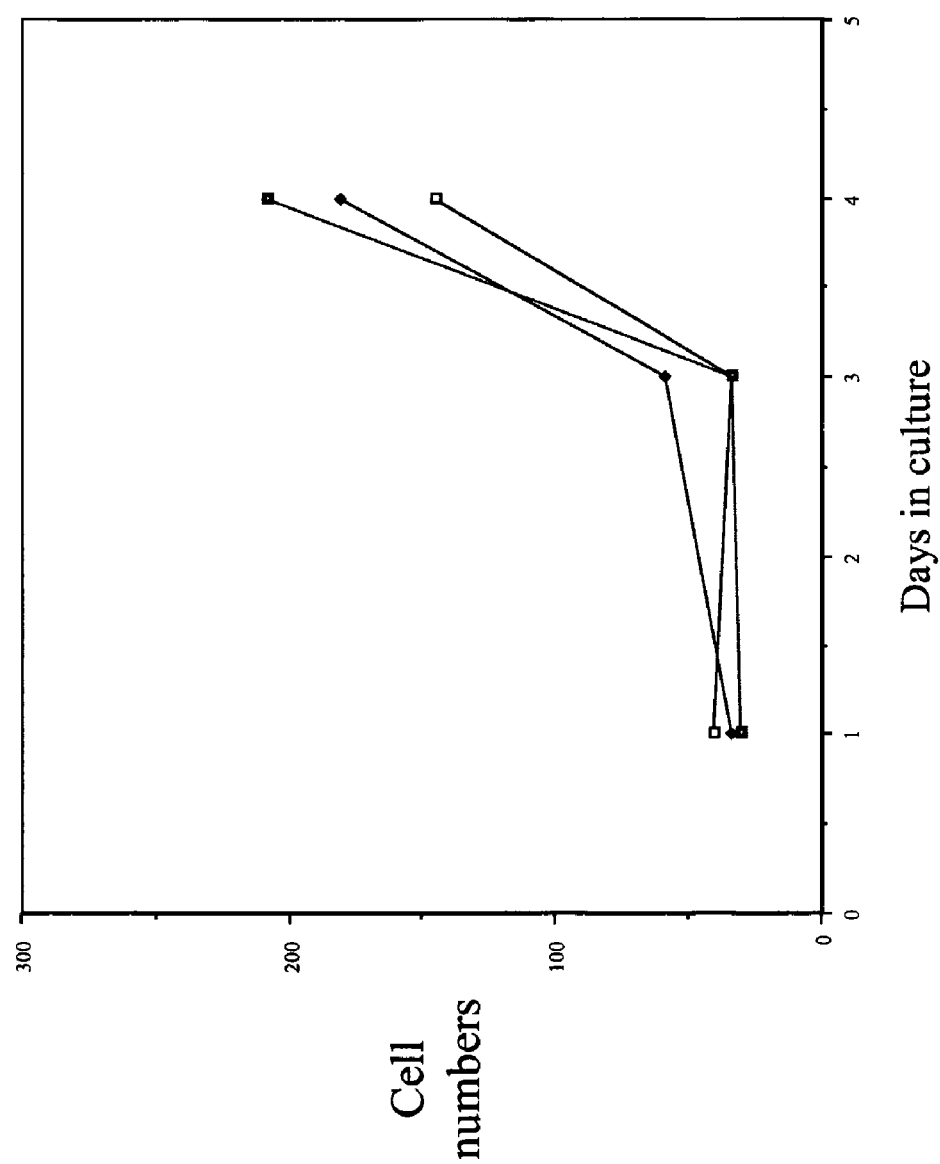

FIG. 7 shows the growth rate of isolated stem cells in culture; cells were seen to divide and proliferate over a period of 4 days; cells isolated with Dynabeads® and antibody SSEA-4 have shown an increase in total number of cells from approximately 50 cells per plate to 150 cells per plate in 4 days of culture; the central area of the plates was determined and a cruciform counting pattern was used; N=10 fields in each culture and numbers on individual days were simply totalled; the data shown in this Figure is the same experiment performed in triplicate.

Figure 8:
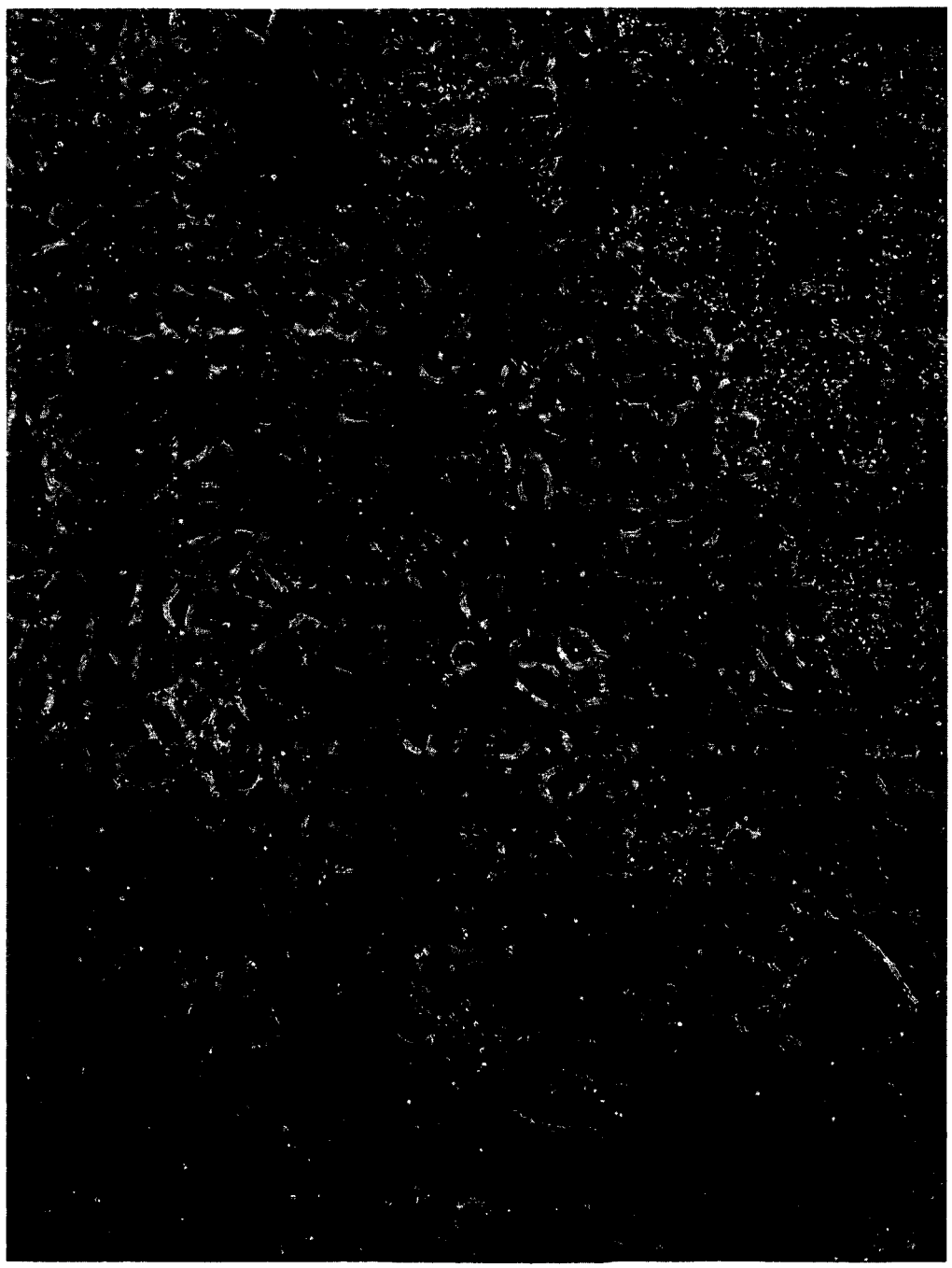

FIG. 8 shows a monolayer of pluripotent cells as obtained from mammalian secretion using an alternative procedure according to the invention.

DETAILED DESCRIPTION OF THE PREFERRED EMBODIMENTS

To determine whether a cell believed to be a stem cell is actually a stem cell, it has historically been necessary to undertake transplantation of the cells of interest into sublethally irradiated mice. If these transplanted cells subsequently locate and repopulate any organs of these mice, the cells in question have been considered to be pluripotent stem cells. However, more recently the identification of extracellular markers for pluripotent stem cells (for example Tra-1-60 and SSEA-4; Chemicon International, Temecula, Calif., US) have enabled the identification of pluripotent (stem) cells without the prolonged process of transplantation.

After washing all cells out of human milk by a repeating the process of gentle centrifugation, aspiration of the supernatant and the resupension of the cells in a buffer or media several times, the stem cells were isolated from a total milk cell population (FIG. 1) using dynabeads according to manufacturers specifications. As buffer Tris-buffered saline solutions (TBS) or phosphate buffered saline solutions (PBS) can be used. In particular, TBS-solutions which are 10 mM in Tris, 150 mM in NaOH and which are adjusted to have a pH around 7.4 can be used. In case of PBS-solutions, those may be 1.1 mM $KH_2PO_4$, 140 mM NaCl, 4.5 mM $Na_2HPO_4.7H_2O$ and 2.7 mM NaCl, and may be adjusted to have a pH around 7.4. As media, Williams or RPMI (Roswell Park Memorial Institute) as available from Sigma Aldrich, US, under the product numbers R6504, R7755, R4130 or W4125, W4128, W1878, can be used. Also possible as media is RPMI from Gibco (CA, US) Cat. No 11875-093.

Stem cell-specific antibodies, e.g. Tra-1-60, Tra 1-81 and/or SSEA-4, both monoclonal, both e.g. available from Chemicon international, CHEMICON International, 28820 Single Oak Drive, Temecula Calif. 92590, were attached to the Dynabeads® for isolation of the progenitor cells. Also possible is the use of haematopoietic cells antibody CD133 (cat# MAB1133) from R&D Systems, Inc CA, US Primitive haematopoietic stem and progenitor cells from peripheral blood have already been isolated using the immuno-magnetic cell separation principles. Research groups using monoclonal-antibody conjugated magnetic particles (CliniMACS System and Reagent AC133 from Miltenyi Biotec) have successfully isolated and cultured CD133 positive cells.

Any stem cell-specific antibody (inclusive of; SSEA-3, SSEA-1 and TRA 1-81 Oct-4, CD133) are incubated with Dynabeads®. Dynabeads® are available from Dynal AS, NO, and are small iron beads, that have an anti-mouse IgG antibody attached to it via a small strand of DNA. Possible are for example Dynabeads® available under the name Dynal CD34. Incubation of the Dynabeads® is carried out for 1 h at room temperature prior to the Dynabeads® being incubated with the cells isolated from milk for 15 minutes at 4° C.

Once the stem cells have bound to the Dynabeads which typically takes about 30 minutes to 1 hour, a magnet is attached to the side of the tube containing the cells/Dynabeads®. Dynabeads® are uniform, polystyrene-based, paramagnetic, beads with 4.5 μm in diameter. The Dynabeads® (with the stem cells attached) are attracted to the magnet, whereas the unbound cells are not and remain in the supernatant. The supernatant is then removed leaving only the cells bound to the Dynabeads® via the stem cell antibody. The cells bound to the Dynabeads® via the stem cell antibody are removed by the addition of Dnase breaking the small strand of DNA. This is called releasing buffer and is part of the Dynal kit 62500 U/ml (15000-20000 U per vial quoted in the instructions). The Dynabeads® are removed by attaching the magnet once more to which the Dynabeads®, no longer attached to the stem cells, are attracted. The supernatant now contains the stem cells which are removed. These stem cells can now be used for any subsequent application as listed above/below.

The isolated progenitor (stem) cells can be cultured on mouse embryo fibroblast feeder cells in Knockout-Dulbecco's modified Eagle's medium. Typically cultivation can be carried out at a temperature of 37° C.

Examples of the use of feeder cells:
Prolonged propagation of human embryonic stem cells is currently achieved by coculture with primary mouse embryonic fibroblasts serving as feeder cells.
Acceleration of the formation of cultured epithelium using the sonic hedgehog expressing feeder cells.
Human adult marrow cells support prolonged expansion of human embryonic stem cells in culture.
Proliferation and maturation of embryonic stem cells into endothelial cells in an in vitro model of vasculogenesis required OP9 feeder cells.
Selective expansion and continuous culture of macrophages from adult pig blood. Macrophages were selectively expanded and continuously cultured from adult pig blood directly into the medium overlaying a feeder layer of STO mouse fibroblasts.
Establishment and characterization of a novel human immature megakaryoblastic leukemia cell line, M-MOK, dependent on fibroblasts for its viability. A novel fibroblast-dependent human immature megakaryoblastic leukemia cell line (M-MOK) was established from the bone marrow of a girl with acute megakaryoblastic leukemia, and its growth was determined to be completely dependent on the presence of human embryonic lung-derived fibroblasts, HEL-O.
In vitro culture of embryonic disc cells from porcine blastocysts using foetal G30 porcine fibroblasts which had been previously irradiated as a feeder layer.
Acute lymphocytic leukemias (ALL) cells of infants and children were found to preferentially survive in coculture with a cloned cell line of endothelial adipose cells (14F1.1) from mouse bone marrow and exhibited extensive growth in the presence of the mouse stromal cells. These ALL cells were strictly dependent upon the mouse stromal clone 14F1.1 and failed to proliferate in the absence of the endothelial adipocytes or with a variety of feeder cells.

Cell Growth

Cells isolated with Dynabeads® and antibody SSEA-4 have shown an increase in total number of cells from approximately 50 cells per plate to 150 cells per plate in 4 days (see FIG. 7).

Methods:

Cell Preparation 150 ml of whole milk is spun for 15 minutes at 2000 rpm to collect cells. Cell pellet is resuspended in approximately 4 ml TBS 1% BSA and centrifuged again for 10 minutes.

Final pellet is resuspended in 200 µl of RPMI 1% FCS.

Bead Preparation

Beads are washed 3× in RPMI 1% foetal calf serum.

Beads coated with primary antibody at a concentration of 1 ul in 500 µl TBS 1% BSA and incubated for 1 hour at room temperature with gentle mixing.

Coated beads separated and washed 3× in 1 ml TBS 1% BSA and transferred to clean tube. Final wash in 1 ml RPMI 1% FCS.

Cell Isolation

200 µl cell preparation added to beads and incubated for 30 min at approximately 4° C.

Following incubation the unbound fraction is discarded.

200 µl RPMI 1% FCS is added to the cell and bead complex which is then gently pipetted to release further unbound matter.

To 200 µl of bead and cell complex add 5 µl releasing buffer and incubate for 15 minutes at 37° C. with gentle mixing.

Vigorously pipette bead plus cell complex to help release cells.

Collect the 200 µl of isolated cell suspension and add to clean Eppendorf.

This cell suspension can then be immediately introduced into the culture system.

Culture Method

Cells were seeded on collagen-coated culture plates.

Following a settling period the supernatant was carefully drawn off to remove contaminants and fresh media added. Cultures were then incubated in plates at 37° C. in a 5% $CO_2$ incubator with medium changes every two days.

Culture Media

William's E medium supplemented with 10% fetal calf serum; $10^{-7}$M dexamethasone (Sigma); Glutamine 2mmol/L ITS+premix containing insulin (6.25 µg/ml), transferrin (6.25 µg/ml), selenious acid (6.25 ng/ml), bovine serum albumin (1.25 mg/ml) and linoleic acid (5.35 µg/ml) from Becton-Dickinson, Bedford, Mass. Penicillin/streptomycin 5,000 µg/ml Fungizone (250 µg/ml)

Antibodies

An example of some of the potential antibodies that can be used in this system are; (All supplied by CHEMICON International, 28820 Single Oak Drive, Temecula Calif. 92590)
SSEA-1 (Cat number MAB4301)
SSEA-3 (MAB4303)
SSEA-4 (MAB4304)
TRA 1-60 (MAB4360)
TRA 1-81 (MAB4381)
haematopoietic cells antibody CD133 (cat# MAB1133) from R&D Systems, Inc.

Buffers
TBS 1%BSA, 10 mM Tris, 150 mM NaOH
RPMI 1% FCS
PBS 1.1 mM $KH_2PO_4$, 140 mM NaCl, 4.5 mM $Na_2HPO_4 7H_2O$ Following purification of the stem cells from human milk, using the extracellular markers for stem cells (Tra-1-60 and SSEA-4) bound to Dynabeads® we cytospun the stem cells onto microscope slides and stained the stem cells using haematoxylin and eosin (FIG. 2). Using these same purified stem cells we have been able to culture the cells (FIG. 3) and demonstrate that these cells do undergo cell division (FIG. 4). Following prolonged culture, we have been able to stain these cells using haematoxylin and eosin (FIG. 5), and have demonstrated that these cells remain stem cells as they continue to bind the stem cell antibodies (Tra-1-60 and SSEA-4) following several months of culture, as visualised by confocal microscopy (FIG. 6). Growth of the isolated cells was also verified, see FIG. 7.

An alternative way of isolation/growth of the pluripotent cells is using a specific combination of growth media by means of which it is possible to grow a monolayer of pluripotent cells that clearly do not look like lactocytes (see FIG. 8). Indeed the grown cells in culture are physically identical to for example liver stem cell cultures. Further classification of these cells by the cellular markers they express and by their gene activity is possible.

This alternative way of isolation or selective growth can be carried out as follows:

Preparation of Matrigel™ Coated Plates:

The Matrigel (commercially available reconstituted basement membrane, BD Matrigel™, BD Biosciences ref-354234) was allowed to defrost slowly on ice. Pipette tips and culture plates were cooled and kept on ice prior to use. 50 µl of the thawed Matrigel was aliqouted and spread with a pipette tip into each of the wells of a 24 well flat bottom microplate and allowed to incubate on ice for 30 minutes. Following this the plates were further incubated for 30 minutes at 37 degrees centigrade in order to set the gel. Once set 1 ml of growth media was aliquoted to each well and the plate returned to the incubator until required (no longer than 5 days).

Growth and Preparation of Cells

Freshly expressed hind milk (approximately 50 ml, hind milk is human breastmilk that is high in fat content and creamy in color; it provides the bulk of the baby's calories and is most responsible for weight gain) was centrifuged to pellet the cells (details as given above).

The cell pellet was washed 2× in RPMI media (RPMI Medium 1640, Gibco ref-108-36) only.

Cells were then plated onto cell culture treated plastic culture dishes in growth media (Cell culture growth media composition: RPMI 1640; Fetal Bovine serum 20%; Insulin 5 µg/ml; Cholera toxin 50 µg/ml; Hydrocortisone 0.5 µg/ml; Penicilin streptomycin fungizone 2×) and allowed to incubate for approximately 14-20 days.

After this period plates showing large colonies and approaching confluence were selected and the cells harvested by trypsinization (Trypsin-EDTA 1×, JRH Bioscience ref=59218).

The harvested cells were washed 1× in growth media and plated onto Matrigel™ coated plates at a density approximately 1500 cells/ml.

After around 14 days patches of confluent cells can be observed.

Description

The morphology is typically epithelial in that confluent sheets of cells develop and the cells within the colonies are closely associated. The fact that breastmilk derived cells cultured in this manner will proliferate in primary culture and form extensive circular colonies with well defined borders is strongly indicative of cells with progenitor like qualities. That the cells appear undifferentiated and many can be observed to have a large nucleus to cytoplasm ratio is even more evidence for a progenitor like identity.

Specific Materials Used
Cholera toxin (LIST BIOLOGICAL LABORATORIES ref-101B)
Fetal Bovine serum (Invitrogen ref-10099141)
Hydrocortisone (Sigma ref-HO135)
Insulin (Sigma ref-19278)
Pencillin/Strepomycin Fungizone (Scott Scientific ref-17.745E)
MICROPLATE (IWAKI ref-3820-024)
Cell Culture Dish (Corning ref-430165)

Due to the plasticity of the pluripotent stem cells, these isolated cells can be utilised for a multitude of different applications. For example these cells can be;

- used to create tissues for the benefit of the mother and infant (and potentially other individuals), including gene therapy treatments, intrauterine foetal treatments, and the generation of cells, tissue, glands, or organs for the treatment of disease. This includes their use in scientific research, clinical, diagnostic or commercial applications. This can also include the generation of biological compounds including cells, cellular compartments, cellular secretions, cell isolates, nucleotides, deoxyribonucleic acids, amino acids, proteins, glycoproteins, carbohydrates, lipids, hormones, growth factors, and cytokines. Furthermore, this can include the generation of cells as a precursor, or as a consequence, of the generation of tissue, glands or organs for the treatment of disease, tissue regeneration, body enhancement, or cosmetic applications for the following tissues; Olfactory, Auditory, Optical, Lymphatic, Immune, Haematopoietic, Endocrine, Exocrine, Bowel, Gastrointestinal, Peyers Patches, Islets of Langerhans, Skeletal, Muscle, Connective, Vascular, Blood, Skin, Hair, Nails, Mammary, Brain and Central Nervous System, Liver, Heart, Lung, Kidney, Bone, Pancreas, Reproductive.
- stored for future. The subsequent use of these stem cells, or cells differentiated or dedifferentiated could include storage of these stem cells for future use as outlined below. This includes their storage for use in scientific research, clinical, diagnostic or commercial applications.
- used for cell culture, whether this be for propagation of these same stem cells, or for the differentiation or dedifferentiation of these stem cells into another cell type. This includes their use in scientific research, clinical, diagnostic or commercial applications.
- used for cloning. The subsequent use of these stem cells, or cells differentiated or dedifferentiated from these stem cells could be used to generate clones, whether embryonic or whole animal. This includes their use in scientific research, clinical, diagnostic or commercial applications.
- used for scientific research. The subsequent use of these stem cells, or cells differentiated or dedifferentiated from these stem cells could be used in scientific research. This can include the generation of biological compounds including cells, cellular compartments, cellular secretions, cell isolates, nucleotides, deoxyribonucleic acids, amino acids, proteins, glycoproteins, carbohydrates, lipids, hormones, growth factors, and cytokines. In addition this could include the generation of cells as a precursor, or as a consequence, of the generation of tissue, glands or organs for the treatment of disease, tissue regeneration, body enhancement, or cosmetic applications for the following tissues; Olfactory, Auditory, Optical, Lymphatic, Immune, Haematopoietic, Endocrine, Exocrine, Bowel, Gastrointestinal, Peyers Patches, Islets of Langerhans, Skeletal, Muscle, Connective, Vascular, Blood, Skin, Hair, Nails, Mammary, Brain and Central Nervous System, Liver, Heart, Lung, Kidney, Bone, Pancreas, Reproductive.
- used for clinical, diagnostic or commercial applications. The subsequent use of these stem cells, or cells differentiated or dedifferentiated from these stem cells could be used in clinical, diagnostic or commercial applications. This can include the generation of biological compounds including cells, cellular compartments, cellular secretions, cell isolates, nucleotides, deoxyribonucleic acids, amino acids, proteins, glycoproteins, carbohydrates, lipids, hormones, growth factors, and cytokines. In addition this could include the generation of cells as a precursor, or as a consequence, of the generation of tissue, glands or organs for the treatment of disease, tissue regeneration, body enhancement, or cosmetic applications for the following tissues; Olfactory, Auditory, Optical, Lymphatic, Immune, Haematopoietic, Endocrine, Exocrine, Bowel, Gastrointestinal, Peyers Patches, Islets of Langerhans, Skeletal, Muscle, Connective, Vascular, Blood, Skin, Hair, Nails, Mammary, Brain and Central Nervous System, Liver, Heart, Lung, Kidney, Bone, Pancreas, Reproductive.
- used for bioengineering. The subsequent use of these stem cells, or cells differentiated or dedifferentiated from these stem cells could be used to generate any other cell type in the human body. These cells, tissues, or organs could then be used for cosmetic/reconstructive surgery, organ/tissue transplantation or the generation of cells/tissue/organs for a third party. This can include the generation of biological compounds including cells, cellular compartments, cellular secretions, cell isolates, nucleotides, deoxyribonucleic acids, amino acids, proteins, glycoproteins, carbohydrates, lipids, hormones, growth factors, and cytokines. In addition this could include the generation of cells as a precursor, or as a consequence, of the generation of tissue, glands or organs for the treatment of disease, tissue regeneration, body enhancement, or cosmetic applications for the following tissues; Olfactory, Auditory, Optical, Lymphatic, Immune, Haematopoietic, Endocrine, Exocrine, Bowel, Gastrointestinal, Peyers Patches, Islets of Langerhans, Skeletal, Muscle, Connective, Vascular, Blood, Skin, Hair, Nails, Mammary, Brain and Central Nervous System, Liver, Heart, Lung, Kidney, Bone, Pancreas, Reproductive.
- used for lactoengineering. The subsequent use of these stem cells, or cells differentiated or dedifferentiated from these stem cells could be used to generate biological compounds of milk including cells, cellular compartments, cellular secretions, cell isolates, nucleotides, deoxyribonucleic acids, amino acids, proteins, glycoproteins, carbohydrates, lipids, hormones, growth factors, and cytokines.
- breast tissue regeneration. The subsequent use of these stem cells, or cells differentiated or dedifferentiated from these stem cells could be used to generate breast tissue.
- breast reconstructive surgery. This regenerated tissue as above could then be used for reconstructive breast surgery.
- breast cosmetic surgery This regenerated tissue as above could then be used for cosmetic breast surgery.

exocrine gland tissue regeneration and/or surgery. The subsequent use of these stem cells, or cells differentiated or dedifferentiated from these stem cells could be used to generate exocrine gland tissue, which in turn, could be used for the regeneration or replacement of exocrine glands.

the generation of biological compounds including cells, cellular compartments, cellular secretions, cell isolates, nucleotides, deoxyribonucleic acids, amino acids, proteins, glycoproteins, carbohydrates, lipids, hormones, growth factors, and cytokines.

The invention claimed is:

1. A method for isolating cells having stem cell-like characteristics of SSEA-4 and Tra-1-60 marker expression from human milk, wherein the milk is subjected to centrifugation, wherein following centrifugation the cells having stem-cell like characteristics are separated from a cell pellet by suspending the cell pellet in a growth medium and immuno-isolating the cells having stem-cell like characteristics with magnetic beads and stem cell-specific antibodies.

2. A method according to claim 1, wherein the cells having stem-cell like characteristics are isolated from a cellular portion of the milk that is separated from an acellular portion.

3. A method according to claim 1, wherein human secretory epithelial cells and leucocytes, and microorganisms are removed from the milk.

4. A method according to claim 1, wherein the cells having stem-cell like characteristics are isolated from milk isolated during lactating periods wherein said lactating periods are selected from the group consisting of the period after beginning of individual feeding, and the early lactation period.

5. A method according to claim 1, wherein in a first step cellular components are washed out of the milk and retained, in a second step said cellular components are stained with antibodies to the stem cell markers, and in a third step the cells having stem-cell like characteristics are separated from the other cells directly or indirectly by means of the attached antibodies.

6. A method according to claim 5, wherein the antibody-stained cells having stem-cell like characteristics are attached to beads and the cells having stem-cell like characteristics are isolated using said beads, wherein when said beads are small iron beads, said beads are isolated using a magnet, and wherein subsequently the beads or the antibodies or both are removed from the cells having stem-cell like characteristics.

7. A method according to claim 6, wherein the beads are removed using an enzyme selected from the group consisting of DNase, Proteinase, and RNase.

8. A method according to claim 1, wherein the cells having stem-cell like characteristics are cultured without using a fibroblast feeder layer.

9. A method according to claim 1, wherein in
(i) a first step the milk is subjected to centrifugation leaving a fat layer on top, a protein and carbohydrate rich supernatant beneath it, and at the bottom a pellet of cells;
(ii) in a second step the fat fraction and supernatant are removed;
(iii) in a third step a volume of a buffer or cell culture media is added and the cells are resuspended in the buffer or media and centrifuged as in the first step and repeating this step 3 or 4 times, leaving a substantially pure cell pellet; and
(iv) in a fourth step separating the cells having stem cell-like characteristics from the cell pellet.

10. A method according to claim 9, wherein the cells having stem-cell like characteristics are separated from the cell pellet in that:
(iv-1) the cell pellet is suspended in cell culture media;
(iv-2) this suspension is incubated for 15 minutes at 4° C. with stem cell-specific antibodies linked to magnetic beads via a small strand of DNA;
(iv-3) a magnet is positioned in proximity to the suspension, whereby cells having stem-cell like characteristics that have bound to the magnetic beads attract the cells connected with the beads to the magnet, whereas unbound cells are not attracted by the magnet and remain in the supernatant; and
(iv-4) the supernatant is removed, leaving only the cells having stem-cell like characteristics bound to the beads via the stem cell-specific antibodies.

11. A method according to claim 10, wherein thereafter:
(v) cells having stem-cell like characteristics bound to the beads via the stem cell-specific antibodies are removed by a cleavage means, wherein when the antibody is attached to the beads via small strand of DNA, said cleavage means is a DNase,
(vi) the beads are removed by positioning the magnet to attract the beads, no longer attached to the cells having stem-cell like characteristics, to it; and
(vii) removing the supernatant containing the isolated cells having stem-cell like characteristics.

12. A method according to claim 1, wherein the cells, following centrifugation, are incubated in a growth media that is permissive for growth of progenitor cells, stem cells or lactocyte growth.

13. A method according to claim 12, wherein in
(i) a first step the unfractionated milk is subjected to centrifugation leaving a fat layer on top, a protein and carbohydrate rich supernatant beneath it, and at the bottom a pellet of cells;
(ii) in a second step, the cell pellet is washed in cell culture media;
(iii) in a third step the cells comprising the cell pellet are plated onto a cell culture vessel in bacteriocidal, fungicidal or both bacteriocidal and fungicidal growth media and incubated for 10-30 days and thereafter,
(iv) the cells are harvested and washed using buffer or growth media, and
(v) the harvested cells are plated onto a reconstituted basement membrane preparation.

14. A method according to claim 13, wherein in step (v) the solubulized basement membrane preparation is extracted from EHS mouse sarcoma.

15. The method of claim 1, wherein the cells are isolated directly or indirectly from colostrum or mature milk.

16. The method of claim 1, wherein the cells are isolated during at least one time period that is selected from the group consisting of a non-pregnant period, a pregnant period, a lactating period, and an involuting period.

* * * * *